US00PP22317P2

(12) United States Plant Patent
Kordes

(10) Patent No.: US PP22,317 P2
(45) Date of Patent: Dec. 13, 2011

(54) HYBRID TEA ROSE PLANT NAMED 'KORERISIO'

(50) Latin Name: *Rosa hybrida*
Varietal Denomination: KORerisio

(75) Inventor: Tim-Hermann Kordes, Klein Offenseth-Sparrieshoop (DE)

(73) Assignee: W. Kordes' Sohne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/660,462

(22) Filed: Feb. 25, 2010

(51) Int. Cl.
*A01H 5/00* (2006.01)

(52) U.S. Cl. ..... Plt./132

(58) Field of Classification Search ..... Plt./130, Plt./132, 133, 137, 141
See application file for complete search history.

*Primary Examiner* — June Hwu

(57) ABSTRACT

A new and distinct variety of rose with long lasting, novel flowers which exhibit light pink centers and dark pink edges, and attractive foliage with good disease resistance. It exhibits uniform growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORerisio'.

CROSS REFERENCES AND FEDERAL R&D STATEMENT:

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1998. The crossing was between MEImucas, a non-patented rose and an un-named, unpatented rose seedling from the same breeder.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORerisio'.

SUMMARY OF THE INVENTION

The new rose plant may be distinguished from its seed parent, MEImucas, by the following combination of characteristics:

1. The flower shape of 'MEImucas' is high-centered, while the flower shape of 'KORerisio' is quartered.
2. The flower color of 'MEImucas' is orange-pink, while the flower color of 'KORerisio' is a blend of pinks, with a light pink center and a dark pink edge.

The new rose plant may be distinguished from its pollen parent, an un-named seedling, by the following combination of characteristics:

1. The 'un-named seedling' has no fragrance, while 'KORerisio' has a strong fragrance.
2. The flower color of the 'un-named seedling' is uniformly pink, while the flower color of 'KORerisio' is a blend of pinks, with a light pink center and dark pink edges.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORerisio' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORerisio' was selected in May 2005 from the seedling beds to be asexually propagated for further evaluation. The first asexual propagation of 'KORerisio' was done by budding to seedling understocks in July, 2007 at the inventor's nursery in Offenseth-Sparrieshoop, Germany.

This initial and other subsequent propagations conducted in controlled environments demonstrate that 'KORerisio' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORerisio'.

DETAILED BOTANICAL DESCRIPTION

The following is a description of 'KORerisio', as observed growing in October, 2009 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORtiglo', a rose variety from the same inventor described and illustrated in U.S. Plant Pat. No. 19,385 and issued on Oct. 28, 2008 are compared to 'KORerisio' in Chart 1.

CHART 1

| Characteristic | 'KORerisio' | 'KORtiglo' |
|---|---|---|
| Flower Color | Light pink center, Dark pink edges | Honey-yellow to apricot |
| Fragrance | Strong, pleasant fragrance | Light fragrance |
| Petal Count | 50-60 | 100-120 |

Parents:

*Seed parent.*—'MEImucas'.

*Pollen parent.*—'Un-named seedling'.

Classification:

*Botanical classification.*—*Rosa hybrida* 'KORerisio'.

*Commercial classification.*—Hybrid Tea rose.

FLOWER AND FLOWER BUD

Blooming habit: Recurrent.

Flower bud:

*Size.*—Upon opening, 35 mm in length from base of receptacle to end of bud and 25 mm diameter at its widest point.

*Bud form.*—Medium. Pointed ovoid.

*Bud color.*—As sepals first unfold, bud color is Orange Group 27C. When ¼ open, the upper surface of petals is Green-Yellow Group 1D, and the lower surface is Yellow-Green Group 154D.

*Sepals.*—Size: Average 40 mm long×15 mm wide. Shape: Sepals generally subulate. Sepal apex is generally cirrose. Weak foliaceous appendages on three of the five sepals. Base is flat at union with receptacle. Quantity: Five. Margins: With Stipitate glands. Surface texture: Inner side: Puberulent pubescence. Outer surface: Puberulent pubescence. Stipitate glands are absent. Color: Upper surface: Yellow-Green Group 144B with intonations of Yellow-Green Group 144D. Lower surface: Yellow-Green Group 144D.

Receptacle:

*Surface.*—Smooth.

*Color.*—Yellow-Green Group N144C.

*Shape.*—Funnel.

*Size.*—10 mm (h)×12 mm (w).

Peduncle:

*Surface.*—Smooth.

*Length.*—45 mm average length.

*Diameter.*—4 mm average diameter.

*Color.*—Yellow-Green Group N144C.

*Strength.*—Strong.

*Borne.*—Multiple flower buds per stem, generally 2 to 4.

Flower bloom:

*Fragrance.*—Moderate.

*Duration.*—On the plant, 14 days. As a cut flower, 10 to 12 days. Senesced petals drop away cleanly.

*Size.*—Large flowered hybrid-tea rose. When open, the average flower diameter is 75 mm and the average flower height is 55 mm.

*Form.*—Shape of flower when viewed from the side: Upon opening, upper part: Convex. Upon opening, lower part: Concave. Open flower, upper part: Flattened convex. Open flower, lower part: Concave.

Color:

*Upon opening, petals.*—Outermost petals: Outer Side: White Group N155D. Intonations of Red Group 47C at petal margin. Inner Side: White Group 155A. Intonations of Red Group 47D at petal margin. Innermost petals: Outer Side: White Group N155D. Inner Side: Green-White Group 157D.

*Upon opening, basal petal spots.*—Basal petal spot, outermost petals: Outer Side: White Group 155C. Inner Side: White Group 155C. Basal petal spot, innermost petals: No distinctive coloration at petal base observed.

*After opening, petals.*—Outermost petals: Outer Side: White Group N155C, with intonations of Red Group 49C at petal margin. Inner Side: Green-White Group 157D, with intonations of Red Group 49D at petal margin. Innermost petals: Outer Side: White Group N155D. Inner Side: White Group 155D.

*After opening, basal petal spots.*—No distinctive coloration at petal base observed. Variegations: None.

General tonality: On open flower: Red Group 36C. No change in the general tonality at the end of the 8$^{th}$ day. Afterwards, general tonality is Red Group 36D.

Petals:

*Petal count.*—Approximately 60 petals under normal conditions.

*Petal reflex.*—Petals reflex slightly.

*Petal edge.*—Ruffled.

*Petal shape.*—Deltoid. Apex shape is round. Shape of base is acute.

*Petal size.*—55 mm long; 45 mm wide.

*Thickness.*—Average.

*Petal arrangement.*—Generally in a regular pattern with overlapping edges.

Petaloids: Present.

*Petaloid count.*—Average of 0-5 per flower.

*Petaloid edge.*—Undulated.

*Petaloid texture.*—Smooth.

*Petaloid shape.*—Obovate.

*Petaloid size.*—Petaloids are 7 mm long and 4 mm wide.

*Petaloid color.*—Color of inner side is White Group N155D. Color of outer side is White Group N155D.

Reproductive organs:

*Pistils.*—Approximately 70 present. Stigmas: Location: Level in position to anthers. Color: Red Group 39A. Styles: Length: 8 mm long. Color: White Group 155A.

*Stamens.*—Approximately 90-110 on average and regularly arranged. Anthers: Size: 3 mm long. Color: Green-Yellow Group 1D. Pollen: Generally Absent. Color: Green-Yellow 1B. Filaments: Color: Green-Yellow 1D. Length: 10 mm.

THE PLANT

Plant growth: Moderately vigorous with a bushy to upright habit. When grown as a budded nursery plant the average plant height is 100-120 cm and the average plant width is 70 cm.

Stems:

*Stem color.*—Young wood: Yellow-Green Group 144A. Older wood: Yellow-Green Group 144B.

*Stem surface.*—Young wood: Smooth. Older wood: Smooth.

Prickles: Present.

*Incidence.*—30 per 10 cm of stem.

*Size.*—Average length: 4 mm.

*Color.*—Immature prickles: Greyed-Red Group 181B. Mature prickles: Greyed-Orange Group 164 B. Senescing to Greyed-Orange Group 164A. Intonations: Greyed-Orange Group 164C.

*Shape.*—Concave.

*Anthocyanin.*—Color Greyed-Red 182A.

Leaves and leaflets: Normally 7 leaflets on normal leaves in middle of the stem.

*Venation pattern.*—Pyramidal net pattern.

*Leaf size.*—120 mm (1)×80 mm (w).

*Quantity.*—Abundant.

*Texture.*—Upper side of leaflet: Semi glossy. Smooth. Under side of leaflet: Matte. Leathery.

*Color, mature foliage.*—Upper Leaf Surface: Yellow-Green Group 146A. Lower Leaf Surface: Yellow-Green Group 146D.

*Color, juvenile foliage.*—Upper Leaf Surface: Green Group 137A. Lower Leaf Surface: Yellow-Green Group 146B.

*Anthocyanin intonation.*—Present. Location: Intonations present on juvenile leaf margins and developing leaves.

Stipules:

*Size.*—25 mm long. 12 mm between the tips of the stipule. Main body of stipule 10 mm in width.

*Shape.*—Base: Winged. Apex: Pointed.

*Stipule color.*—Yellow-Green Group 144B. Anthocyanin Greyed-Red Group 181B.

*Presence of stipitate glands.*—Present on margins.

*Margins.*—With stipitate glands.

Petiole:

*Length.*—17 mm.

*Diameter.*—2 mm.

*Petiole color.*—Yellow-Green Group 144B. Anthocyanin present on juvenile tissue. Color: Greyed-Red Group 182 B.

*Underneath.*—A few small prickles underneath.

*Stipitate glands.*—Limited numbers of stipitate glands on margins.

Petiole rachis:

*Length.*—60 mm.

*Diameter.*—2 mm.

*Color.*—Yellow-Green Group 144B. Anthocyanin present on juvenile tissue.

*Margins.*—With stipitate glands.

*Prickles.*—Numerous prickles underneath.

*Stipitate glands.*—Stipitate glands present on margins.

Leaflets:

*Size.*—Average size of terminal leaflet is 45 mm (1)×35 mm (w).

*Shape.*—Ovate. Base: Rounded. Apex: Acute.

*Margins.*—Serrated.

*Texture.*—Thick.

Hips/seed formation: None observed.

Winter hardiness: To date, the variety has been grown successfully in Zone 5.

Disease resistance: Above average resistance to Powdery mildew (*Sphaerotheca pannosa*), rust (*P. disciflorum*), blackspot (*Diplocarpon rosae*), and *Botrytis* (*Botrytis cinerea*) diseases under normal growing conditions.

I claim:

1. A new and distinct variety of rose plant as herein illustrated and described.

* * * * *

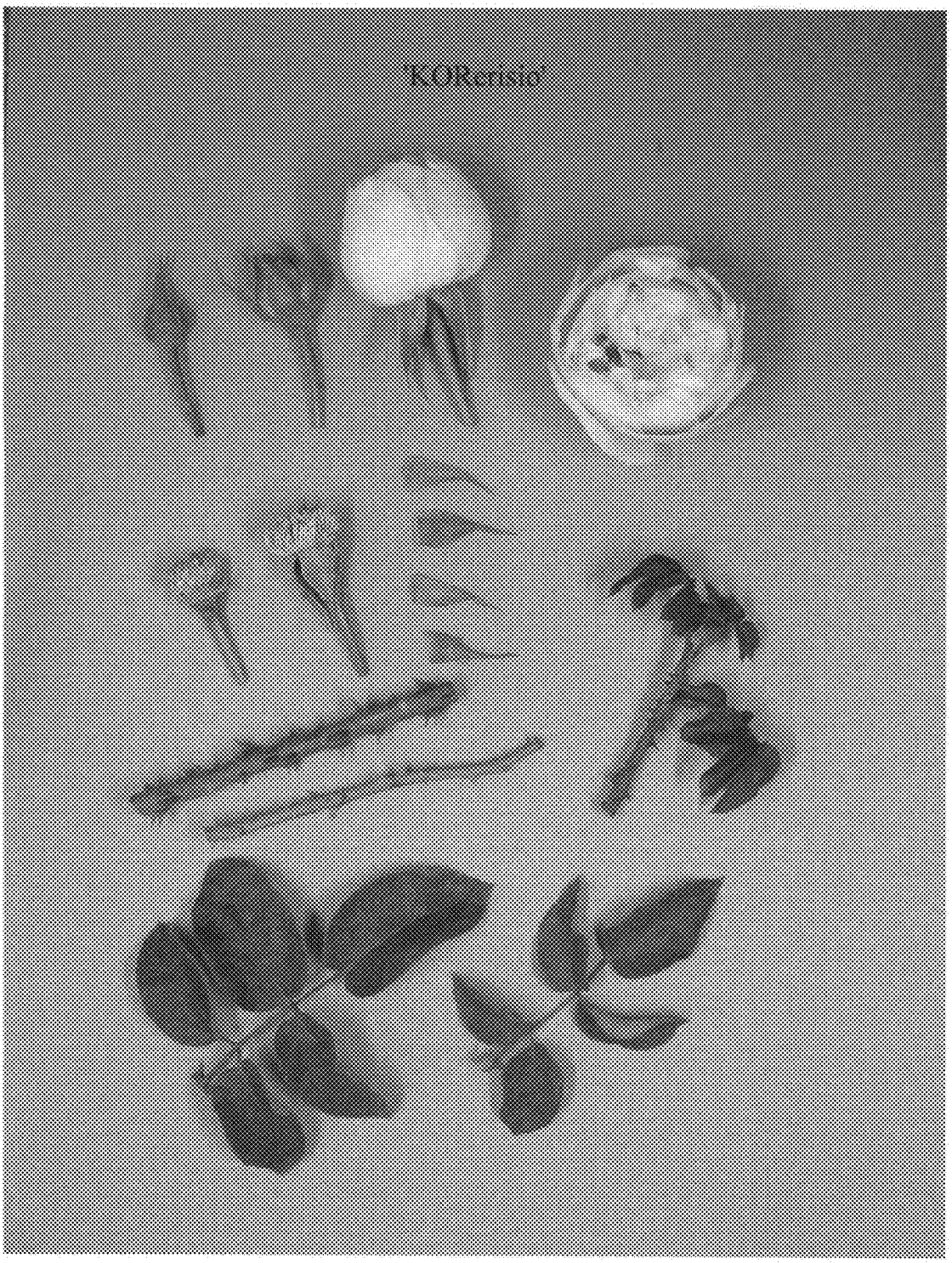
'KORerisio'